United States Patent [19]

Bruce et al.

[11] Patent Number: 5,961,519
[45] Date of Patent: *Oct. 5, 1999

[54] BURR HOLE COVER FOR CRANIAL SURGERY

[75] Inventors: Robert Bruce, Ventura, Calif.; Ronald T. Zellem, Hendersonville, Tenn.

[73] Assignee: Kinamed, Inc., Newbury Park, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/834,055

[22] Filed: Apr. 11, 1997

[51] Int. Cl.$^6$ ........................................ A61B 17/80
[52] U.S. Cl. ........................ 606/69; 606/129; 606/213
[58] Field of Search ................... 606/69, 70, 71, 606/129, 130, 61, 213

[56] References Cited

U.S. PATENT DOCUMENTS

| | | | |
|---|---|---|---|
| 1,105,105 | 7/1914 | Sherman | 606/69 |
| 4,503,848 | 3/1985 | Casper et al. | 606/69 |
| 5,201,737 | 4/1993 | Leibinger et al. | 606/69 |
| 5,364,399 | 11/1994 | Lowery et al. | 606/69 |
| 5,578,036 | 11/1996 | Stone et al. | 606/69 |

OTHER PUBLICATIONS

The Definitive Neuro Fixation System; Anspach Fixation Systems (Brochure), (No date).

*Primary Examiner*—Michael Buiz
*Assistant Examiner*—David O. Reip
*Attorney, Agent, or Firm*—Oppenheimer Wolff & Donnelly LLP

[57] ABSTRACT

The burr hole cover includes a thin plate having radial arms in an exemplary embodiment. Each arm has a distal end opening for receiving a fastener for attaching the plate to the cranium. An enlarged access passageway through the plate, preferably at the plate's center provides a passageway for an intracranial monitoring tube. The passageway is elongated to allow the tube to pass through the burr hole cover at a gentle angle.

5 Claims, 2 Drawing Sheets

BURR HOLE COVER FOR CRANIAL SURGERY

TECHNICAL FIELD

The present invention relates to a burr hole cover that may be used for providing cranial access for an intracranial monitoring tube following cranial surgery.

BACKGROUND OF THE INVENTION

Cranial surgery requires access to a specific area of the brain. To gain such access, the surgeon must form a brain access flap in the cranium of the patient. Typically, the surgeon drills three spaced burr holes through the cranium at the apexes of an imaginary triangularly shaped access area. Because of the curvature of the cranium, the access flap is not a true planar triangle. The flap also may not be triangular but may be rectangular or be other polygonal or irregular shapes. If the access flap has more than three apexes, the surgeon usually drills a burr hole at each apex. Some surgeons use a single burr hole.

After cutting the burr holes, the surgeon then cuts though the cranium using a high-speed cutting tool. The tool has a guard that is inserted in the burr hole under the bone and above the dura. When the surgeon uses multiple burr holes, the cuts extend between the burr holes to form a removable cranial flap. Surgeons using a single burr hole cut the flap freehand in a pattern out from the hole and then returning to the hole. Once the surgeon has formed the flap, he or she carefully removes the flap to provide the necessary access to the brain.

These surgical procedures involve forming holes and gaps in the cranium to expose the brain. Therefore, each surgical operation requires a closing procedures to reattach the flap and to cover the burr holes. Burr hole covers that cover the burr hole and attach the flap are known. The Leibinger E-Z Flap is an example of such a burr hole cover. See also FIG. 1, which depicts a prior art burr hole cover. Although described in more detail in the "Detailed Description of the Exemplary Embodiments," prior art burr hole covers are described briefly here.

Burr hole covers consist of titanium, and many have a shape similar to some types of snow flakes. Some have a central body with five or six projecting arms. The distal ends of the arms usually have screw-receiving openings through which a cranial bone screw extends to attach the cover to the cranium. Some covers have very short arms extending from a larger central body. In others, screw-receiving openings are at the periphery of the central body so that the cover essentially has no arms. Often the arms or the screw-receiving openings are asymmetrically spaced. The asymmetry allows the surgeon to rotate the cover until all screw holes can be over good bone. The cover also has openings that speed healing.

Cranial surgery procedures sometimes require the monitoring of intra-cranial pressures following surgery. In this regard, the surgeon typically inserts a monitoring tube next to the burr hole cover. This tube then remains in place for a sufficient period of time to complete the monitoring purposes. Monitoring typically takes from a few days to a week or more. When the patient no longer requires monitoring, the surgeon pulls the tube from the cranial cavity.

Both the insertion and removal of the tube presents challenges. The tube contains delicate fiber optics that can break easily if the tube bends during placement. The fiber optics also can break while the tube is in place over the course of several days. Also, the tube may snag and become stuck when removed. Therefore, having a new and improved burr hole cover that eases the placement, protection and removal of an intracranial monitoring tube safely and efficiently is highly desirable.

Another problem with prior art burr hole covers is that they project above the normal cranial surface. Though the projection may be slight, some patients can feel the cover through the scalp with their fingers. Making the transition from the cover to the cranial bone as gradual as possible is desirable.

SUMMARY OF THE INVENTION

Therefore, the principal object of the present invention is to provide a new and improved burr hole cover that facilitates the placement and removal of an intracranial monitoring tube.

Another object of the present invention is to provide a new and improved burr hole cover that substantially reduces or eliminates cosmetic deformities from the covers.

Briefly, the present invention's burr hole cover includes a thin plate having a plurality of distal screw-receiving openings about its periphery or at the ends of radial arms. Each screw-receiving opening can receive a fastener for the rigid fixation of the cover to the cranium or to a flap of cranial bone being replaced after surgery. An enlarged, elongated access opening through the plate near the center of the cover provides a passageway for an intracranial monitoring tube. Beveled edges surround the access passageway to allow the monitoring tube to lie against the outside of the cover without passing over a sharp edge in the cover. The elongated nature of the access passageway also allows the tube to lie flat. The burr hole cover's edges are beveled for a smooth transition between the cover and the cranium.

DETAILED DESCRIPTION OF THE EXEMPLARY EMBODIMENTS

Figure 4:
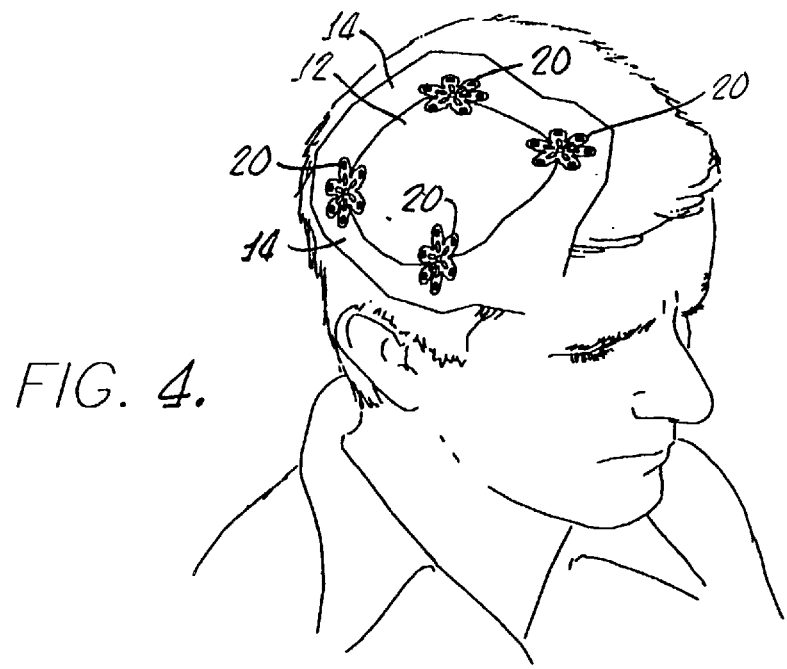
FIG. 4 is a pictorial view illustrating four burr hole covers fixing a cranial flap to the cranium.
Figure 5:
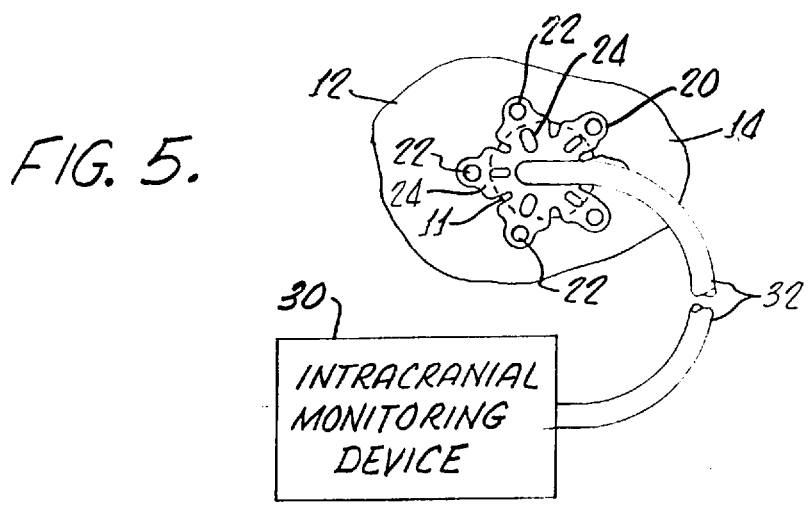
FIG. 5 is a diagrammatic view of intracranial monitoring system, illustrating its use with the burr hole cover of the present invention.

FIG. 4, which shows a patient following surgery, illustrates the type of surgery with which one uses the burr hole cover of the present invention. For access to the brain, the surgeon typically drills one or more burr holes. In the FIG. 4 illustration, the surgeon had drilled four burr holes. Although the holes themselves are not visible in FIG. 4, they are under the burr hole covers 20. FIG. 5 shows such a burr hole 11.

After drilling the holes, the surgeon uses a high-speed drill with a rotating cutter to cut the cranium between the burr holes. Normally, the high-speed cutter has a guard that is inserted through the burr hole and against the dura. The guard protects the dura and brain from the cutting blade. When finished cutting between all burr holes, the surgeon removes the cranial flap 12 from the rest of the cranium 14 for access to the brain. Some surgeons use a single burr hole and use the high-speed cutter to cut a freehand flap.

After the surgery on the brain is finished, the surgeon replaces the flap 12. As is known, the surgeon fixes the flap with burr hole covers 20 over each burr hole (FIG. 4). FIG. 5 shows how burr hole cover 20 fits over the burr hole. The surgeon rotates the cover such that two or three screw openings 22 at the distal ends of arms 24 are over good bone of the flap 12. The remaining screw holes are over the remaining cranial bone 14. Screws (not shown) are then inserted through the screw openings 22, and the burr hole cover is fastened to the flap 12 and the rest of the cranium 14. That fixes the flap to the rest of the cranium. Though not shown, the surgeon may use additional fasteners along the edge between the flap 12 and the remaining cranium 14 to help secure the flap and cranium together.

Figure 1:
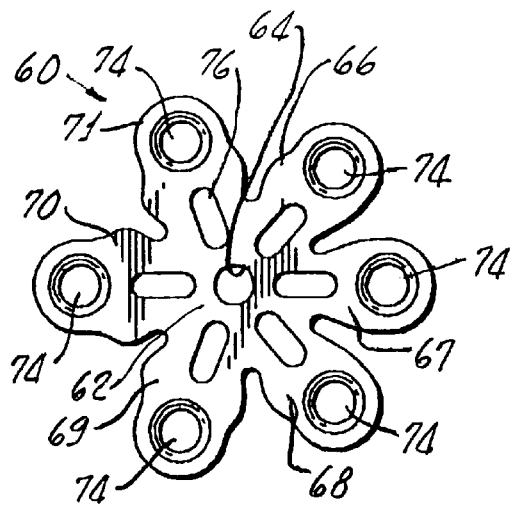
FIG. 1 is a top plan view of a prior art burr hole cover.

FIG. 1 shows a prior art burr hole cover 60. The cover 60 includes a generally round and low profile plate 62. The plate has a centrally disposed burr hole ventilation aperture or hole 64. The cover 60 also includes six spaced-apart arms 66–71. Screw holes 74 extend through the distal end of each arm. As FIG. 1 shows, arms 69–71 are larger than arms 66–68. Therefore, the burr hole cover 60 is asymmetrical.

Burr hole covers may achieve asymmetry in other ways. Instead of having six equally-spaced arms, there can be five arms. Although other numbers of arms may work, five or six arms are best. Also, irrespective of the number of arms, the arms need not be equally spaced. Asymmetry allows the surgeon to align the screw openings 74 with good bone of the flap 12 and the intact cranium 14. Changing the position of the screw openings 74 can avoid the edges of the cranial flap 12. By having the screw openings 74 at the end of arms 66–71, the surgeon can shape the burr hole cover to match the contours of the cranium.

FIG. 1 shows one type of burr hole cover with arms 66–71. The cover may not have distinct arms. If so, the screw-receiving openings would be along the outside of the central section 62 of the cover.

Burr hole cover 60 also has spaced-apart vent slots 76 (FIG. 1) along with its centrally-located vent hole 64. The cover also may have additional holes or slots. The vent slots and holes facilitate healing.

Figure 2:
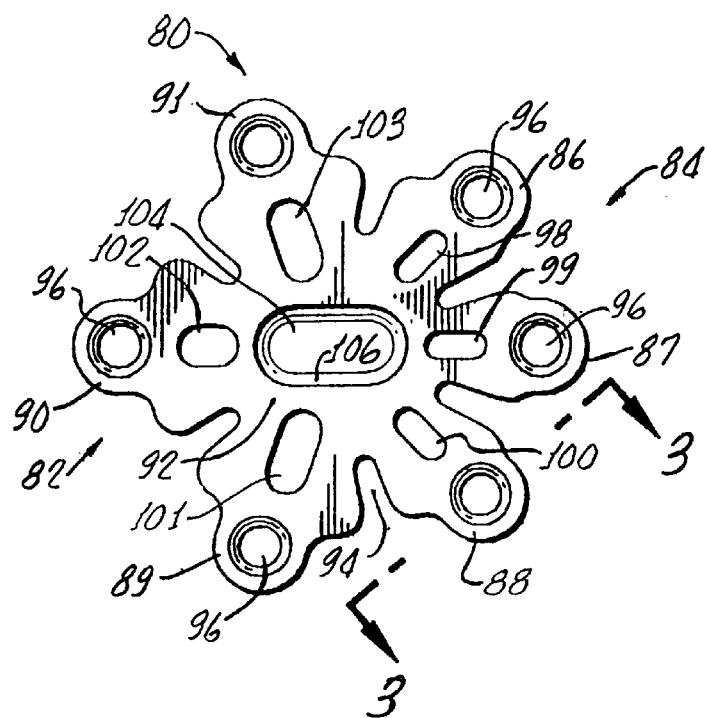
FIG. 2 is a top plan view illustrating one exemplary embodiment of the present invention.

FIG. 2 shows an exemplary embodiment of the present invention. There, the burr hole cover 80 is asymmetrical. Its left side portion 82 is larger than the right side portion 84. In the drawings, left and right are relative. Rotating the cover 80 180° reverses the right and left sides. The burr hole cover 80 includes a set of arms 86–91 extending from the central region 92. One would not see distinct arms if there were no spaces 94 extending into the central region 92.

Each arm has a distal end fastener receiving hole 96 and vent slots 98–103. The slots may be of different sizes. Compare slot 102 with slot 99 or 103. Slots improve patient healing and can be used to control the arms' rigidity to conform to the contour of the cranium.

The burr hole cover 80 (FIG. 2) includes a large centrally disposed monitoring tube receiving slot 104. To accommodate monitoring slot 104, some vent slots may be smaller than others. Thus, vent slot 102 in the FIG. 2 exemplary embodiment is smaller than the adjacent vent slots 103 or 101. Since slot 99 is already small and is the same size as adjacent slots 98 and 100, it is not made smaller.

The asymmetry means that the surgeon can rotate the burr hole cover 80 (about an axis through the page) to achieve better positions of some screw holes 96 relative to the cranial flap 12 and the remaining cranial bone 14. Therefore, no screw-receiving opening 96 is too close to the edge between the flap and the cranium. This leaves enough space on the bone away from an edge for the screw to hold the bone properly. The surgeon also can position the screw-receiving openings advantageously to "good" bone. With the FIG. 2 embodiment, the screw-receiving openings 96 on the smaller right side of the burr hole cover would attach to the flap 12. The screw-receiving openings on the left side would attach to the remaining cranial bone 14.

Figure 3:
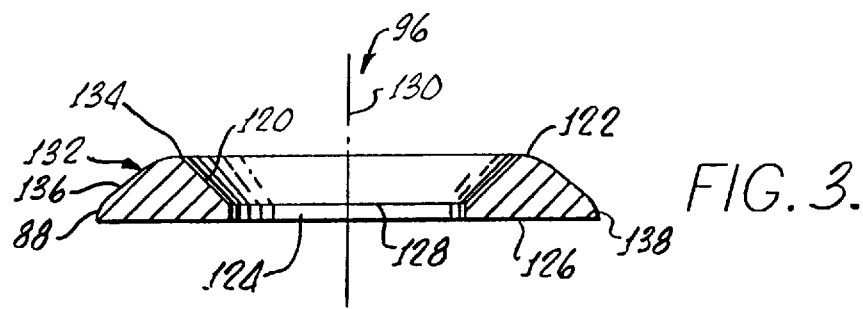
FIG. 3 is a cross-sectional view of the cranial bone cover of FIG. 3 taken substantially through plane 3—3 in FIG. 2.

Each screw-receiving opening 74 is similar to each other. As FIG. 3 shows, screw-receiving opening 96 includes a tapered recess 120 at an upper surface 122 of the arm 88. The screw-receiving opening also has a cylindrical recess 124 at a lower surface 126 of the arm 88. The tapered recess 120 and the cylindrical recess 124 intersect at an inner lip 128 and are aligned along a common longitudinal axis 130.

The arm 88 has smooth beveled edges, such as the edge 132 (FIG. 3). The beveled edge 132 includes successively a smooth rounded portion 134 that commences at the upper surface 136, an intermediate straight portion 138, and another smooth rounded portion 140 that terminates at the lower surface 126 of the arm. The periphery of the burr hole cover also has rounded or beveled edges. Smooth edges help reduce patient discomfort from contact by the scalp tissue. The beveled edges also make the burr hole cover 80 less noticeable to the touch once the healing process has been completed. Other types of cranial surgical devices have used rounded as opposed to beveled edges, but they are more noticeable to the touch.

FIG. 5, shows a prior art intracranial monitoring system 30 that includes a monitoring tube 32. The tube terminates in a transducer (not shown) that rests inside the cranium. The transducer transmits data through a fiber optic cable within monitoring tube 32. It is important that the tube not bend too much, or the fiber optic cable will be damaged. The previously-mention elongated aperture 104 accommodates the monitoring tube 32. Because the intracranial monitoring tube receiving aperture 104 is elongated, the monitoring tube 32 passes through the burr hole cover at a gentle angle. Accordingly, it does not bend sharply. Further, the slot-like shape for the aperture 104 aligns the monitoring tube 32 and allows the tube to pass through the burr hole cover at a gentle angle.

The elongated aperture 104 has a sloped sidewall 106 (FIG. 2). The sloped sidewall allows monitoring tube 32 to lie flat along the outside of the aperture 104. More complex shapes for the sloping are contemplated. For example, one normally would not want a sharp edge at the intersection between the sloped sidewall 106 and either the top or bottom surface of the burr hole cover. Internal sharp edges in the sloped sidewalls also should be avoided.

Eventually, the surgeon removes the monitoring tube. If it catches on the intracranial monitoring tube receiving aperture 104, the tube would pull on the burr hole cover. That could cause pain or discomfort. Fortunately, the elongated nature of the aperture 104 allows the tube to be removed at a gentle angle without catching on the aperture.

The tube receiving aperture 104 is centrally located on burr hole cover 20 in the exemplary embodiment. Although not a preferred embodiment, the aperture could be off-center or partially along an arm. One could modify the arm's size or shape to accommodate such an aperture.

Many modifications and alternate embodiments will occur to those skilled in the art. Therefore, applicants intend that the invention is limited only in terms of the appended claims.

I claim:

1. A burr hole cover for attachment to bone, comprising:

a thin plate for covering a surgically formed cranial burr hole, the thin plate having a geometric center and a central region around the geometric center and a plurality of arms extending radially from the central region;

at least one vent slot extending through a portion of each arm;

a screw receiving opening on at least one arm; and an elongated receiving aperture through the central region of the thin plate and extending over the geometric center for providing an unobstructed passage for a long, thin device;

wherein at least one arm of the plurality of arms is wider circumferentially than one other arm of the plurality of arms and wherein the at least one vent slot on the wider arm is larger than the at least one vent slot on the one other arm.

2. The burr hole cover according to claim 1, wherein the thin plate has a top surface facing away from the bone and a bottom surface opposite the top surface, the elongated receiving aperture having a side wall, the side wall having an outside dimension and the outside dimension of the side wall being larger near the top surface of the thin plate than the outside dimension of the side wall near the bottom surface.

3. The burr hole cover according to claim 1 wherein each arm of the plurality of arms has a distal end with a screw receiving opening, and wherein the at least one vent slot on each arm is located proximally to the screw receiving opening and spaced from the elongated aperture.

4. A burr hole cover for attachment to bone, comprising:

a thin plate for covering a surgically formed cranial burr hole, the thin plate having a geometric center and a central region around the geometric center and a plurality of arms extending radially from the central region, wherein the plurality of arms are spaced unevenly circumferentially about the central region of the thin plate;

a screw receiving opening on at least one arm; and an elongated receiving aperture through the central region of the thin plate and extending over the geometric center for providing an unobstructed passage for a long, thin device.

5. A burr hole cover for attachment to bone, comprising:

a thin plate for covering a surgically formed cranial burr hole, the thin plate having a central region and a plurality of arms extending radially from the central region;

at least one vent slot extending through a portion of each arm;

at least one arm of the plurality of arms being wider circumferentially than one other arm; and the vent slot on the wider arm being larger then the vent slot on the one other arm;

wherein the thin plate has a center, the cover further comprising a receiving aperture in the thin plate, the receiving aperture having a length and a width, the length being greater than the width, the center being within the receiving aperture.

* * * * *